United States Patent

Töpfl et al.

Patent Number: 4,602,936
Date of Patent: Jul. 29, 1986

[54] HERBICIDAL SULFONYLUREAS

[75] Inventors: Werner Töpfl, Dornach, Switzerland; Georg Pissiotas, Lörrach, Fed. Rep. of Germany

[73] Assignee: Ciba-Geigy Corporation, Ardsley, N.Y.

[21] Appl. No.: 645,635

[22] Filed: Aug. 30, 1984

[30] Foreign Application Priority Data

Sep. 9, 1983 [CH] Switzerland ............ 4932/83

[51] Int. Cl.⁴ .......... C07D 239/42; C07D 403/14; A01N 47/36
[52] U.S. Cl. .......................... 71/90; 71/92; 71/93; 544/182; 544/208; 544/207; 544/211; 544/212; 544/215; 544/219; 544/238; 544/295; 544/296; 544/320; 544/321; 544/323; 544/324; 544/330; 544/331
[58] Field of Search .......... 544/320, 321, 323, 331, 544/332, 324, 182, 215, 219, 238, 295, 296; 71/92, 90, 91

[56] References Cited

U.S. PATENT DOCUMENTS

| | | | |
|---|---|---|---|
| 4,474,600 | 10/1984 | Aya | 71/92 |
| 4,511,392 | 4/1985 | Rore | 71/90 |

FOREIGN PATENT DOCUMENTS

| | | | |
|---|---|---|---|
| 0044211 | 1/1982 | European Pat. Off. | 71/92 |
| 0044807 | 1/1982 | European Pat. Off. | 71/92 |
| 0044808 | 1/1982 | European Pat. Off. | 71/92 |
| 125205 | 11/1984 | European Pat. Off. | 71/90 |
| 2112783 | 7/1983 | United Kingdom | 71/92 |
| 2112784 | 7/1983 | United Kingdom | 71/92 |
| 2126586 | 3/1984 | United Kingdom | 71/90 |

*Primary Examiner*—Robert Gerstl
*Attorney, Agent, or Firm*—Edward McC. Roberts; Kevin T. Mansfield

[57] ABSTRACT

Substituted N-phenylsulfonyl-N'-pyrimidinylureas and N-phenylsulfonyl-N'-triazinylureas of the general formula

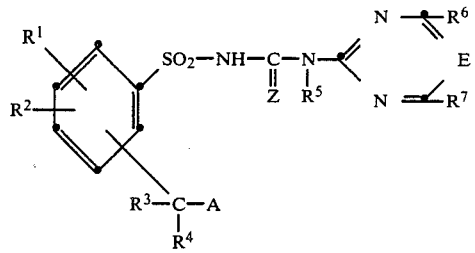

and the salts thereof with amines, alkali metal bases or alkaline earth metal bases, or with quaternary ammonium bases, have good pre- and postemergence selective herbicidal and growth regulating properties.

In the above formula the symbols have the following meanings:

$R^1$ is hydrogen, halogen, nitro, cyano, $C_1$-$C_4$alkyl, $C_1$-$C_4$haloalkyl, $C_1$-$C_4$alkoxy, $C_1$-$C_4$alkylthio, $C_1$-$C_4$alkylsulfinyl, $C_1$-$C_4$alkylsulfonyl, —CO—$R^8$, —$NR^9R^{10}$, —CO—$NR^{11}R^{12}$ or —$SO_2$—$NR^{13}R^{14}$, $R^2$ is hydrogen, halogen, $C_1$-$C_4$alkyl, $C_1$-$C_4$alkoxy, $C_1$-$C_4$alkylthio, $C_1$-$C_4$alkylsulfinyl or $C_1$-$C_4$alkylsulfonyl, $R^3$ is hydrogen, $C_1$-$C_4$alkyl, $C_1$-$C_4$haloalkyl or cyano, $R^4$ is hydrogen or $C_1$-$C_4$alkyl, $R^5$ is hydrogen, $C_1$-$C_4$alkyl or $C_1$-$C_4$alkoxy, $R^6$ and $R^7$ are each independently hydrogen, halogen, $C_1$-$C_4$alkyl, $C_1$-$C_4$alkoxy, $C_1$-$C_4$haloalkyl, $C_1$-$C_4$haloalkoxy, $C_1$-$C_4$alkylthio, $C_1$-$C_4$haloalkylthio, $C_2$-$C_4$alkoxyalkyl, $C_3$-$C_6$cycloalkyl or —$NR^{15}R^{16}$, $R^8$ is hydrogen, $C_1$-$C_4$alkyl, $C_1$-$C_4$haloalkyl, $C_1$-$C_4$alkoxy, $C_1$-$C_4$haloalkoxy, $C_1$-$C_4$alkylthio or $C_2$-$C_4$alkoxyalkoxy, $R^9$, $R^{10}$, $R^{11}$, $R^{12}$, $R^{13}$, $R^{14}$, $R^{15}$ and $R^{16}$ are each independently hydrogen or $C_1$-$C_4$alkyl, A is a radical —Y—$(CH_2)_n$—$R^{17}$ or

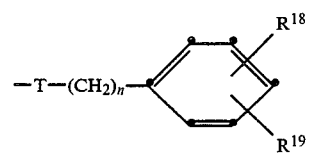

$R^{17}$ is a 5- or 6-membered unsaturated heterocyclic radical, $R^{18}$ and $R^{19}$ are each independently hydrogen, halogen, $C_1$-$C_4$alkyl, $C_1$-$C_4$haloalkyl, $C_1$-$C_4$alkoxy, $C_1$-$C_4$haloalkoxy, nitro or cyano, E is nitrogen or —CH=, Y is oxygen, sulfur or a direct bond, T and Z are each independently oxygen or sulfur, and n is 0 or 1.

22 Claims, No Drawings

HERBICIDAL SULFONYLUREAS

The present invention relates to novel substituted N-phenylsulfonyl-N'-pyrimidinylureas and N-phenylsulfonyl-N'-triazinylureas having herbicidal and plant growth regulating properties, to the preparation thereof, to compositions containing them, and to methods of using them for controlling weeds, preferably selectively, in crops of useful plants, or for regulating and inhibiting plant growth. The invention further relates to novel substituted phenylsulfonamides obtained as intermediates.

Specifically, the invention relates to substituted N-phenylsulfonyl-N'-pyrimidinylureas and N-phenylsulfonyl-N'-triazinylureas of the formula I

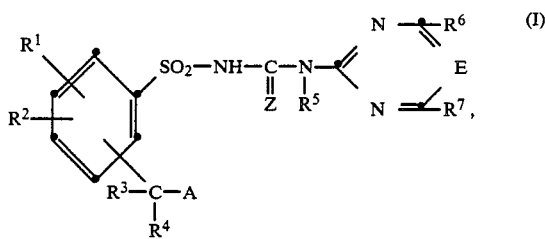

wherein
R[1] is hydrogen, halogen, nitro, cyano, $C_1$–$C_4$alkyl, $C_1$–$C_4$haloalkyl, $C_1$–$C_4$alkoxy, $C_1$–$C_4$alkylthio, $C_1$–$C_4$alkylsulfonyl, $C_1$–$C_4$alkylsulfinyl, —CO—R[8], —NR[9]R[10], —CO—NR[11]R[12] or —SO$_2$—NR[13]R[14], R[2] is hydrogen, halogen, $C_1$–$C_4$alkyl, $C_1$–$C_4$alkoxy, $C_1$–$C_4$alkylthio, $C_1$–$C_4$alkylsulfinyl or $C_1$–$C_4$alkylsulfonyl, R[3] is hydrogen, $C_1$–$C_4$alkyl, $C_1$–$C_4$haloalkyl or cyano, R[4] is hydrogen or $C_1$–$C_4$alkyl, R[5] is hydrogen, $C_1$–$C_4$alkyl or $C_1$–$C_4$alkoxy, R[6] and R[7] are each independently hydrogen, halogen, $C_1$–$C_4$alkyl, $C_1$–$C_4$alkoxy, $C_1$–$C_4$haloalkyl, $C_1$–$C_4$haloalkoxy, $C_1$–$C_4$alkylthio, $C_1$–$C_4$haloalkylthio, $C_2$–$C_4$alkoxyalkyl, $C_3$–$C_6$cycloalkyl or —NR[15]R[16], R[8] is hydrogen, $C_1$–$C_4$alkyl, $C_1$–$C_4$haloalkyl, $C_1$–$C_4$alkoxy, $C_1$–$C_4$haloalkoxy, $C_1$–$C_4$alkylthio or $C_2$–$C_4$alkoxyalkoxy, R[9], R[10], R[11], R[12], R[13], R[14], R[15] and R[16] are each independently hydrogen or $C_1$–$C_4$alkyl, A is a radical —Y—(CH$_2$)$_n$—R[17] or

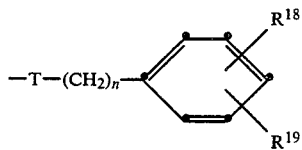

R[17] is a 5- or 6-membered unsaturated heterocyclic radical,

R[18] and R[19] are each independently hydrogen, halogen, $C_1$–$C_4$alkyl, $C_1$–$C_4$haloalkyl, $C_1$–$C_4$alkoxy, $C_1$–$C_4$haloalkoxy, nitro or cyano, E is nitrogen or —CH=, Y is oxygen, sulfur or a direct bond, T and Z are each independently oxygen or sulfur, and n is 0 or 1, and to the salts thereof.

Ureas, triazines and pyrimidines with herbicidal properties are generally known in the art. Sulfonylureas with herbicidal and plant growth-regulating action have recently been described, for example in European patent applications Nos. 44 211, 44 807, 44 808 and in U.K. patent applications Nos. 2 112 783 and 2 112 784.

In the above definitions, alkyl denotes straight-chain or branched alkyl, e.g. methyl, ethyl, n-propyl, isopropyl, or the four butyl isomers.

Alkoxy denotes methoxy, ethoxy, n-propoxy, isopropoxy, the four butoxy isomers, n-amyloxy, isoamyloxy, 2-amyloxy or 3-amyloxy, with methoxy, ethoxy or isopropoxy being preferred.

Alkylthio is e.g. methylthio, ethylthio, n-propylthio, isopropylthio, n-butylthio or n-pentylthio, with methylthio and ethylthio being preferred.

Alkylsulfinyl is e.g. methylsulfinyl, ethylsulfinyl, n-propylsufinyl and n-butylsulfinyl, with methylsulfinyl and ethylsulfinyl being preferred.

Alkylsulfonyl is e.g. methylsulfonyl, ethylsulfonyl or n-propylsulfinyl, with methylsulfonyl and ethylsulfonyl being preferred.

Halogen by itself in the above definitions and as well as moiety of haloalkyl, haloalkoxy or haloalkylthio is fluorine, chlorine and bromine, with fluorine and chlorine being preferred.

The unsaturated 5- or 6-membered heterocycles defined for R[17] comprise within the scope of the present invention for example the following basic ring systems (L is hydrogen or $C_1$–$C_4$alkyl):

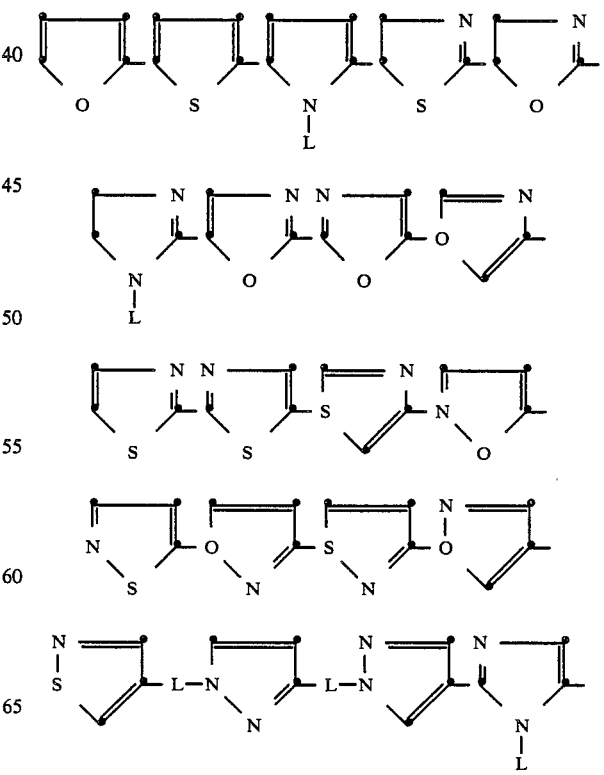

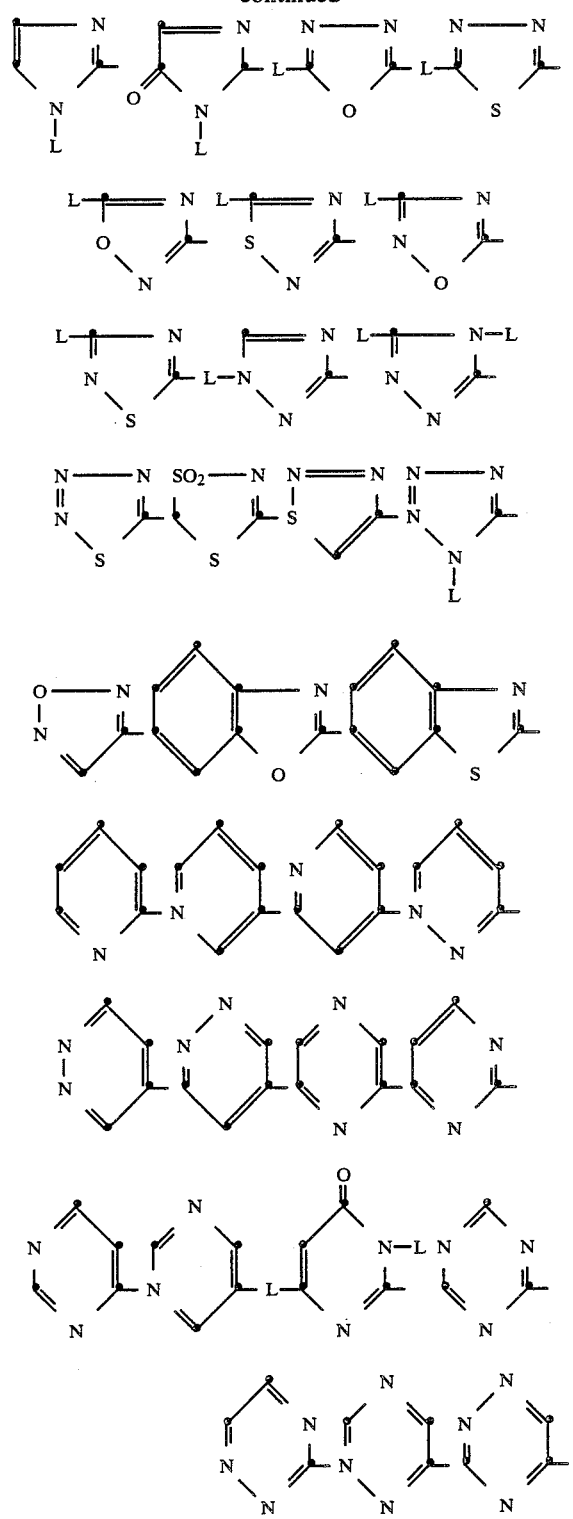
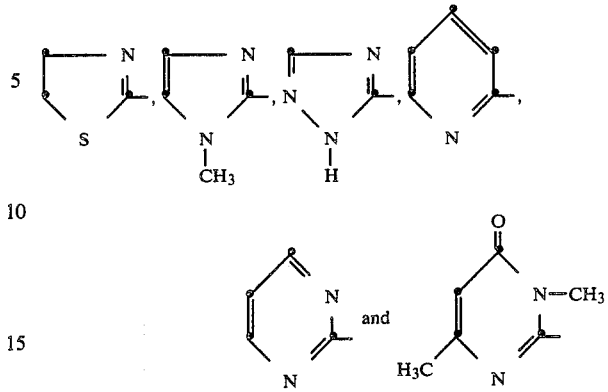

The heterocycles comprised by the definition of $R^{17}$ are all linked through a ring carbon atom to the basic structure of the radical A. The definition also encompasses the partially hydrogenated and/or partially oxidised derivatives.

Preferred heterocycles falling within the definition of $R^{17}$ are:

Alkoxyalkyl radicals are represented by methoxymethyl, ethoxymethyl, methoxyethyl and ethoxyethyl, with methoxyethyl being preferred. Within the scope of this invention, alkoxyalkoxy radicals are methoxymethoxy and ethoxyethoxy. Haloalkyl by itself or as moiety of another substituent such as haloalkoxy or haloalkylthio will generally be chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 1,1,2,3,3-hexafluoropropyl, with fluoromethyl, chloromethyl, difluoromethyl and trifluoromethyl being preferred.

The invention also comprises the salts which the compounds of formula I are able to form with amines, alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine, diethanolamine and 1,4-diazabicyclo[2.2.2]octane being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those wherein either (a) Z is oxygen or
(b) $R^1$ is hydrogen or
(c) $R^2$ is hydrogen or
(d) $R^3$ is hydrogen or
(e) $R^4$ is hydrogen or
(f) $R^5$ is hydrogen or
(g) $R^6$ and $R^7$ are each independently halogen, $C_1$-$C_4$alkyl, $C_1$-$C_4$-alkoxy, di($C_1$-$C_4$)alkylamino or $C_1$–$C_4$haloalkoxy and together contain not more than 4 carbon atoms, or (h) A is the —Y—$(CH_2)_n$—$R^{17}$ group.

Among the compounds of the subgroup (h), especially preferred compounds are those in which n is 0, most particularly those compounds in which A is the —S—$R^{17}$ radical. Examples of particularly preferred radicals —S—$R^{17}$ are 4,5-dihydrothiazol-2-ylthio, 3-methylimidazol-2-ylthio, 1,3,4-triazol-2-ylthio, pyridin-2-ylthio, pyrimidin-2-ylthio or 3H-2,6-dimethyl-3-oxopyrimidin-2-ylthio.

A further preferred subgroup of compounds of the formula I comprises those in which Z is oxygen, $R^1$, $R^2$, $R^3$, $R^4$ and $R^5$ are hydrogen, and each of $R^6$ and $R^7$ is independently halogen, $C_1$–$C_4$alkyl, $C_1$–$C_4$alkoxy, di($C_1$–$C_4$)alkylamino or $C_1$–$C_4$haloalkoxy, and together contain not more than 4 carbon atoms; and especially those in which Z is oxygen, $R^1$, $R^2$, $R^3$, $R^4$ and $R^5$ are hydrogen, each of $R^6$ and $R^7$ is independently halogen, $C_1$–$C_4$alkyl, $C_1$–$C_4$alkoxy, di($C_1$–$C_4$)alkylamino or $C_1$–$C_4$haloalkoxy, and together contain not more than 4 carbon atoms, and A is the —S—$R^{17}$ radical; and among these compounds, in particular those in which Z is oxygen, $R^1$, $R^2$, $R^3$, $R^4$ and $R^5$ are hydrogen, each of $R^6$ and $R^7$ is independently halogen, $C_1$–$C_4$alkyl, $C_1$–$C_4$alkoxy, di($C_1$–$C_4$)alkylamino or $C_1$–$C_4$haloalkoxy, and together contain not more than 4 carbon atoms, and A is a radical selected from the group consisting of 4,5-dihydrothiazol-2-ylthio, 3-methylimidazol-2-ylthio, 1,3,4-triazol-2-ylthio, pyridin-2-ylthio, pyrimidin-2-ylthio or 3H-2,6-dimethyl-3-oxopyrimidin-2-ylthio.

Representative preferred individual compounds are:
N-[2-(4,5-dihydrothiazol-2-ylthiomethyl)phenylsulfonyl]-N'-(4-methoxy-6-methylpyrimidin-2-yl)urea,
N-[2-(pyridin-2-ylthiomethyl)phenylsulfonyl]-N'-(4-methoxy-6-methyl-1,3,5-triazin-2-yl)urea and
N-[2-(pyrimidin-2-ylthiomethyl)phenylsulfonyl]-N'-(4-methoxy-6-methylpyrimidin-2-yl)urea.

The preparation of the compounds of the formula I is generally carried out by the following methods.

A first process for the preparation of compounds of the formula I comprises reacting a substituted phenylsulfonamide of the formula II

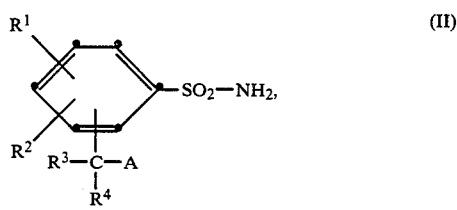

wherein $R^1$, $R^2$, $R^3$, $R^4$ and A are as defined for formula I, with an N-pyrimidinylcarbamate or N-triazinylcarbamate of the formula III

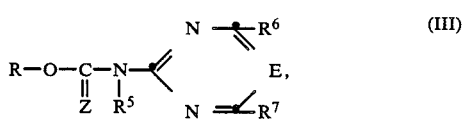

wherein E, $R^5$, $R^6$, $R^7$ and Z are as defined for formula I and R is phenyl, alkyl or substituted phenyl, in the presence of a base.

A second process for the preparation of compounds of the formula I comprises reacting a substituted N-phenylsulfonylcarbamate of the formula IV

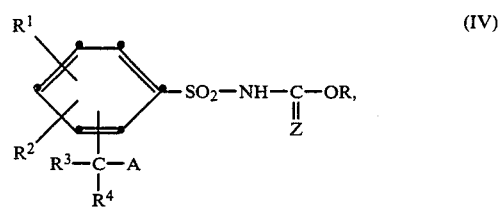

wherein A, $R^1$, $R^2$, $R^3$, $R^4$ and Z are as defined for formula I and R is phenyl, alkyl or substituted phenyl, with an aminopyrimidine or aminotriazine of the formula V

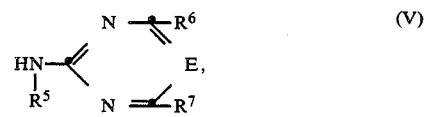

wherein E, $R^5$, $R^6$ and $R^7$ are as defined for formula I.

Finally, the compounds of formula I, in which Y is not a direct bond, can also be prepared by reacting either a sulfonylurea of the formula VI

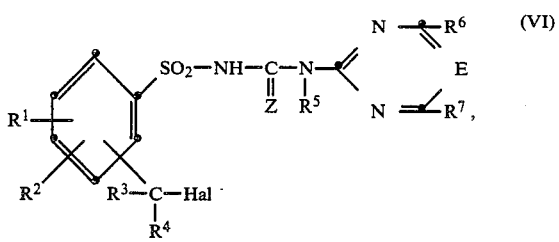

wherein $R^1$, $R^2$, $R^3$, $R^4$, $R^5$, $R^6$, $R^7$, E and Z are as defined for formula I and Hal is halogen, preferably bromine or chlorine, with an alcohol or a mercaptan of the formula VII or VIII

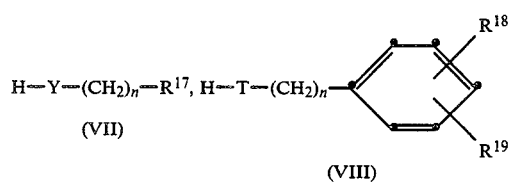

wherein $R^{17}$, $R^{18}$, $R^{19}$, n and T are as defined for formula I and Y is oxygen or sulfur, in the presence of a base; or by reacting a compound of the formula IX

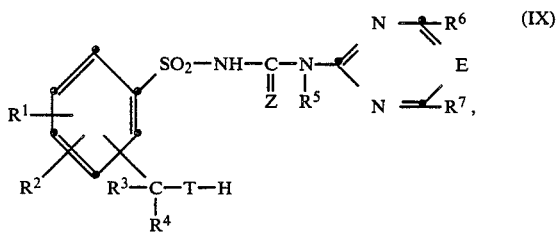

wherein $R^1$, $R^2$, $R^3$, $R^4$, $R^5$, $R^6$, $R^7$, E and Z are as defined for formula I, with a halogen compound of the formula X or XI

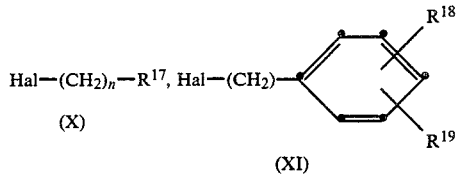

wherein $R^{17}$, $R^{18}$, $R^{19}$ and n are as defined for formula I and Hal is halogen, preferably bromine or chlorine, in the presence of a base.

If desired, the ureas of formula I so obtained can be converted into addition salts with amines, alkali metal hydroxides or alkaline earth metal hydroxides, or with quaternary ammonium bases. This conversion is carried out e.g. by reacting the compounds of formula I with the equimolar amount of a base and removing the solvent by evaporation.

It is convenient to carry out these reactions for obtaining compounds of formula I in aprotic, inert organic solvents. Examples of such solvents are: hydrocarbons such as benzene, toluene, xylene or cyclohexane; chlorinated hydrocarbons such as methylene chloride, chloroform, carbon tetrachloride, or chlorobenzene; ethers such as diethyl ether, ethylene glycol dimethyl ether, diethylene glycol dimethyl ether, tetrahydrofuran or dioxan; nitriles such as acetonitrile or propionitrile; amides such as dimethylformamide, diethylformamide or N-methylpyrrolidinone. The reaction temperatures are preferably in the range from $-20°$ to $+120°$ C. The coupling reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst. Preferred bases are tertiary amines such as trimethylamine, triethylamine, quinuclidine, 1,4-diazabicyclo[2,2,2]octane, 1,5-diazabicyclo[4,3,0]-non-5-ene or 1,8-diazabicyclo[5,4,0]undec-7-ene. However, the bases employed may also be inorganic bases, e.g. hydrides such as sodium hydride and calcium hydride, hydroxides such as sodium hydroxide and potassium hydroxide, carbonates such as sodium and potassium carbonate, or bicarbonates such as potassium and sodium bicarbonate.

The final products of formula I can be isolated by concentrating the reaction mixture and/or removing the solvent by evaporation, and by recrystallisation or by triturating the solid residue in a solvent in which it is poorly soluble, such as an ether, an aromatic hydrocarbon or a chlorinated hydrocarbon.

The intermediates of formulae II are novel and have been specially developed for the synthesis of compounds of the formula I. Accordingly, they constitute an object of the present invention.

The novel intermediates of the formula II are prepared by different methods. Thus the compounds of the subformulae IIa and IIb

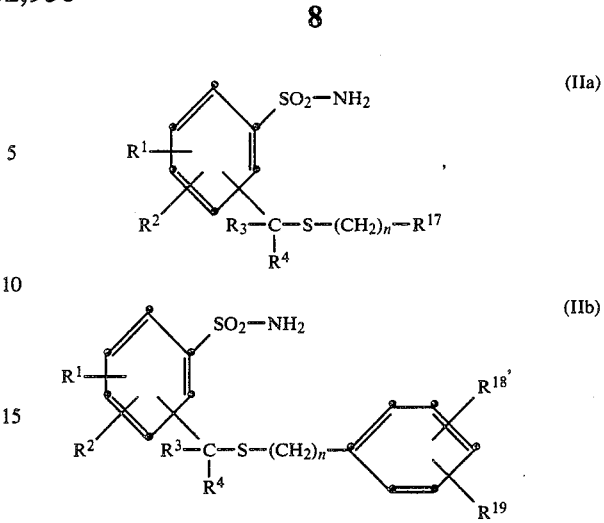

wherein $R^1$, $R^2$, $R^3$, $R^4$, $R^{17}$, $R^{18}$, $R^{19}$ and n are as defined for formula I, are prepared by reacting a phenylsulfonamide of the formula XII

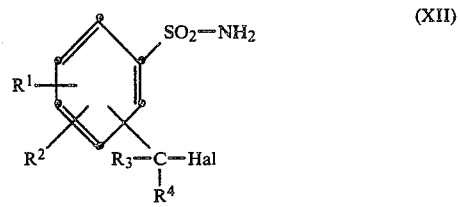

wherein $R^1$, $R^2$, $R^3$ and $R^4$ are as defined for formula I and Hal is halogen, preferably bromine or chlorine, with a mercaptan of the formula XIII or XIV

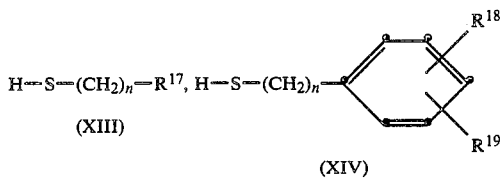

wherein $R^{17}$, $R^{18}$, $R^{19}$ and n are as defined for formula I, in the presence of a base.

The compounds of the subformulae IIc and IId

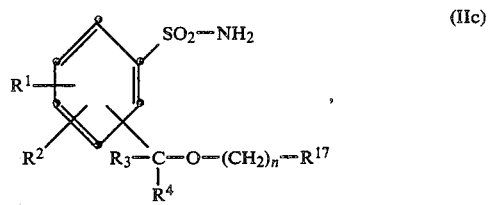

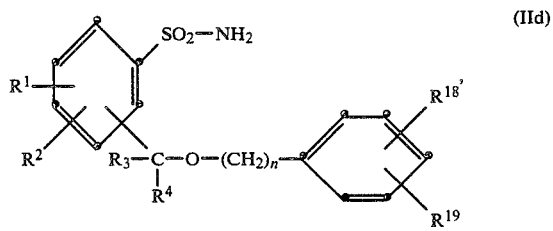

wherein $R^1$, $R^2$, $R^3$, $R^4$, $R^{17}$, $R^{18}$, $R^{19}$ and n are as defined for formula I, are prepared by reacting either (a) a compound of the formula XV

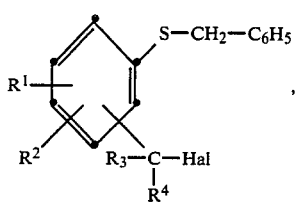
(XV)

wherein $R^1$, $R^2$, $R^3$ and $R^4$ are as defined for formula I and Hal is halogen, preferably bromine or chlorine, with an alcohol of the formula XVI or XVII

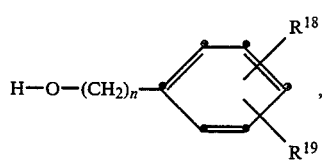
(XVI)

(XVII)

wherein $R^{17}$, $R^{18}$, $R^{19}$ and n are as defined for formula I, in the presence of a base, or (b) reacting a compound of the formula XVIII

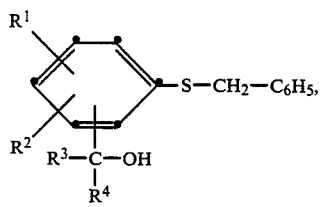
(XVIII)

wherein $R^1$, $R^2$, $R^3$ and $R^4$ are as defined for formula I, with a halide of the formula XIX or XX

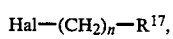
(XIX)

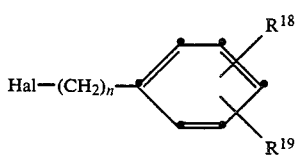
(XX)

wherein $R^{17}$, $R^{18}$, $R^{19}$ and n are as defined for formula I and Hal is halogen, preferably bromine or chlorine, in the presence of a base, and converting the intermediate of the formula XXI or XXII

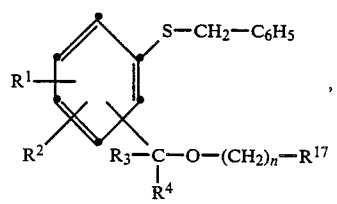
(XXI)

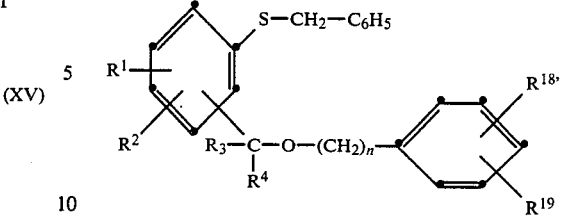
(XXII)

wherein $R^1$, $R^2$, $R^3$, $R^4$, A and n are as defined for formula I, into the sulfonamide of the formula IIc or IId by treatment with chlorine gas and subsequently with ammonia.

The sulfonylcarbamates of the formula IV, which are also novel, are obtained by reacting the sulfonamides of the formula II with a dicarbonate in the presence of a base. Similar processes are described in Japanese Pat. No. 61 169.

The starting aminopyrimidines and aminotriazines of the formula V and corresponding phenylcarbamates of the formula III have either long been known in the art or are described in European patent application No. 70804, or they can be prepared by known methods from compounds disclosed therein.

The starting compounds of the formula VI are described in EP-A No. 44209 or they can be obtained by a similar procedure.

The compounds of the formulae VII, VIII, IX, X, XI, XII, XIII, XIV, XV, XVI, XVII, XVIII, XIX and XX are known or they can be prepared by methods analogous to known ones.

The compounds of the subformulae IIe

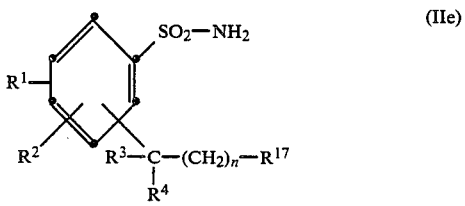
(IIe)

are prepared by methods which are known per se for synthesising heterocycles which are bonded through carbon atoms.

The following synthesis schemes for the preparation of representative individual compounds of the formula IIe are appended below by way of example (L is hydrogen or $C_1$-$C_4$ alkyl):

scheme 1:

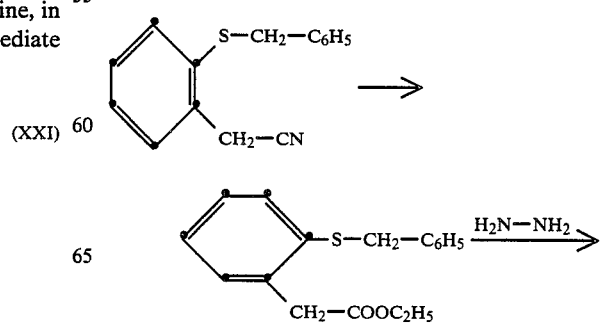

-continued
scheme 1:
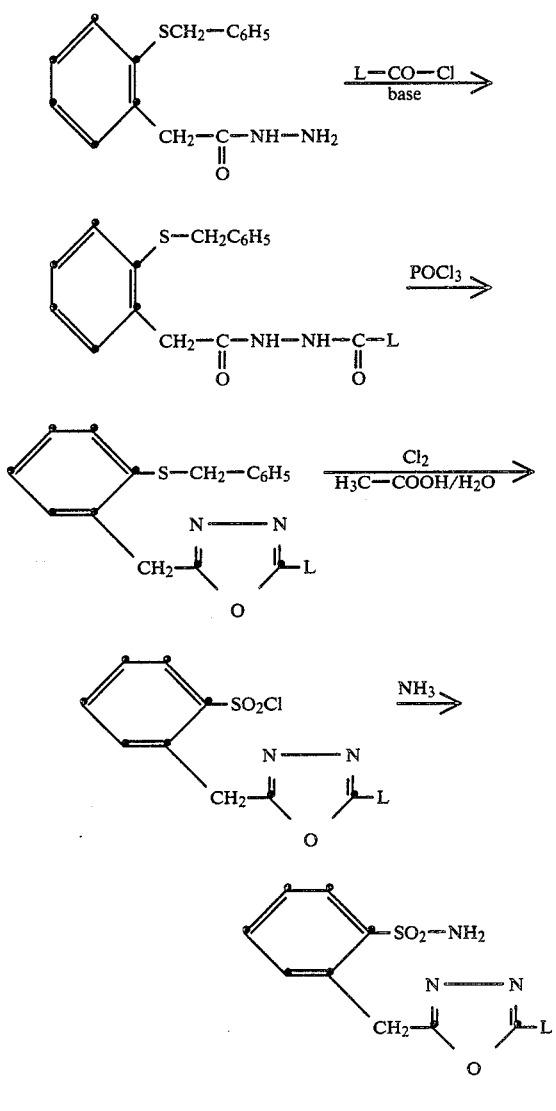
scheme 2:
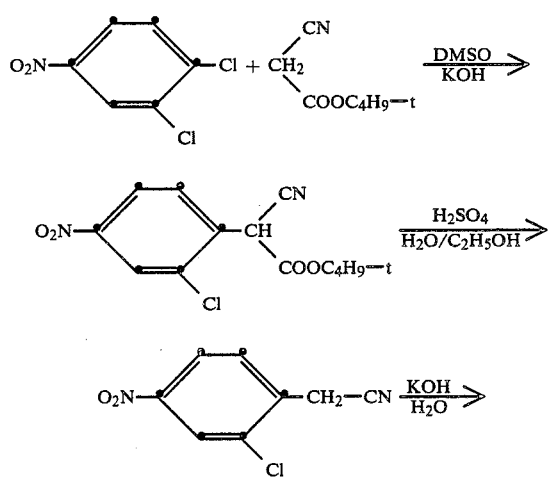
-continued
scheme 2:
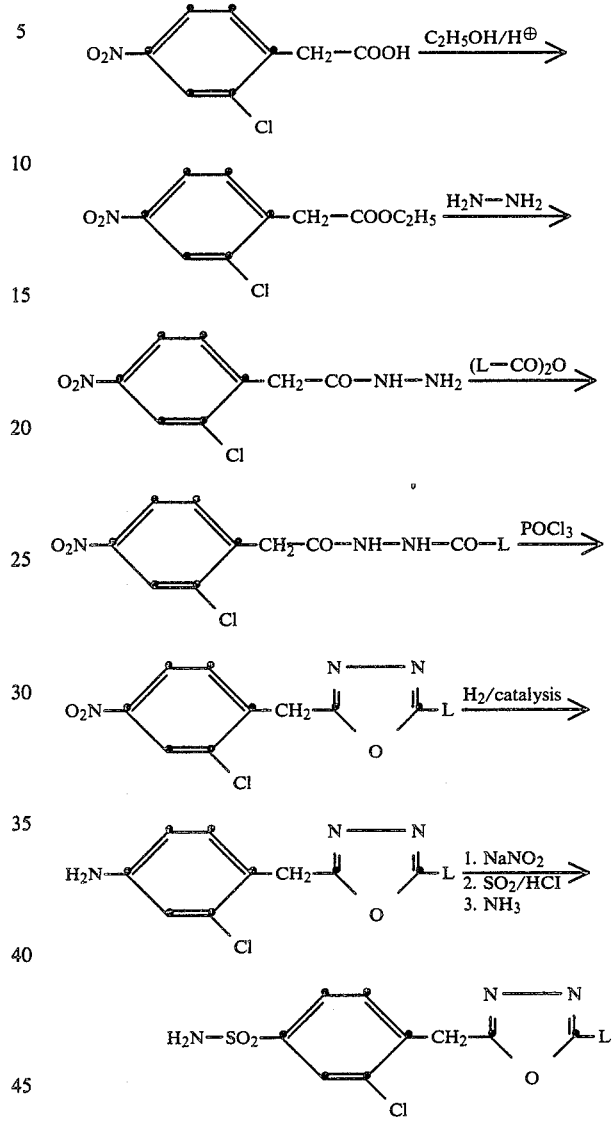
scheme 3:
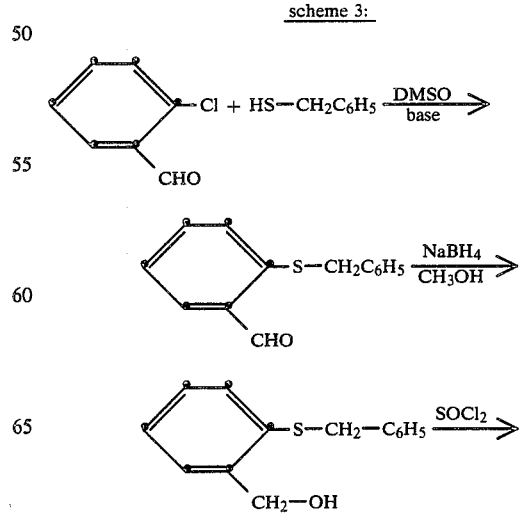

13
-continued
scheme 3:
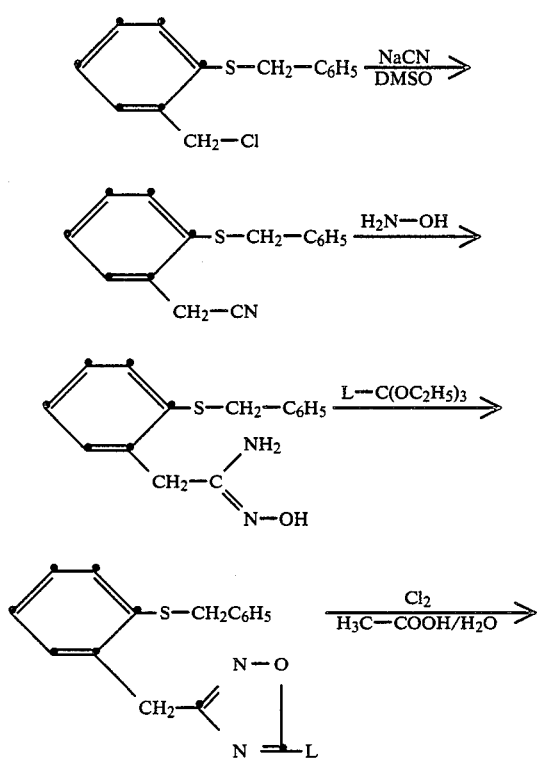
scheme 4:
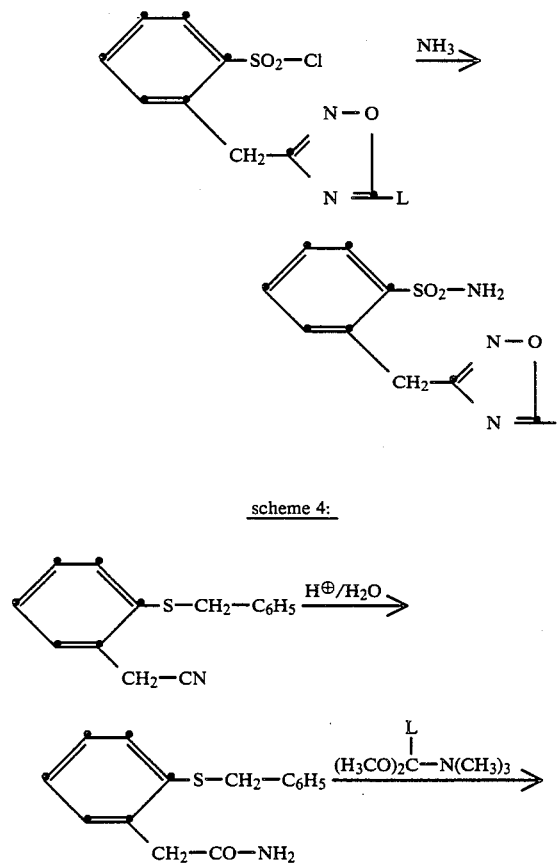
14
-continued
scheme 4:
scheme 5:
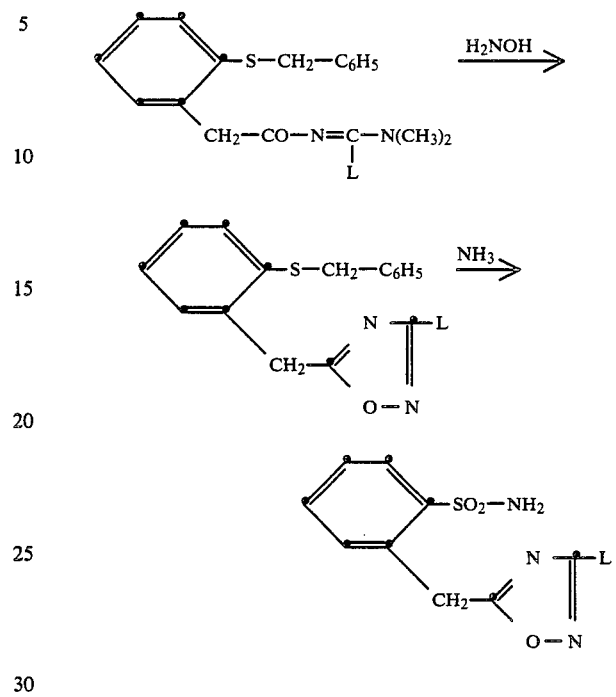

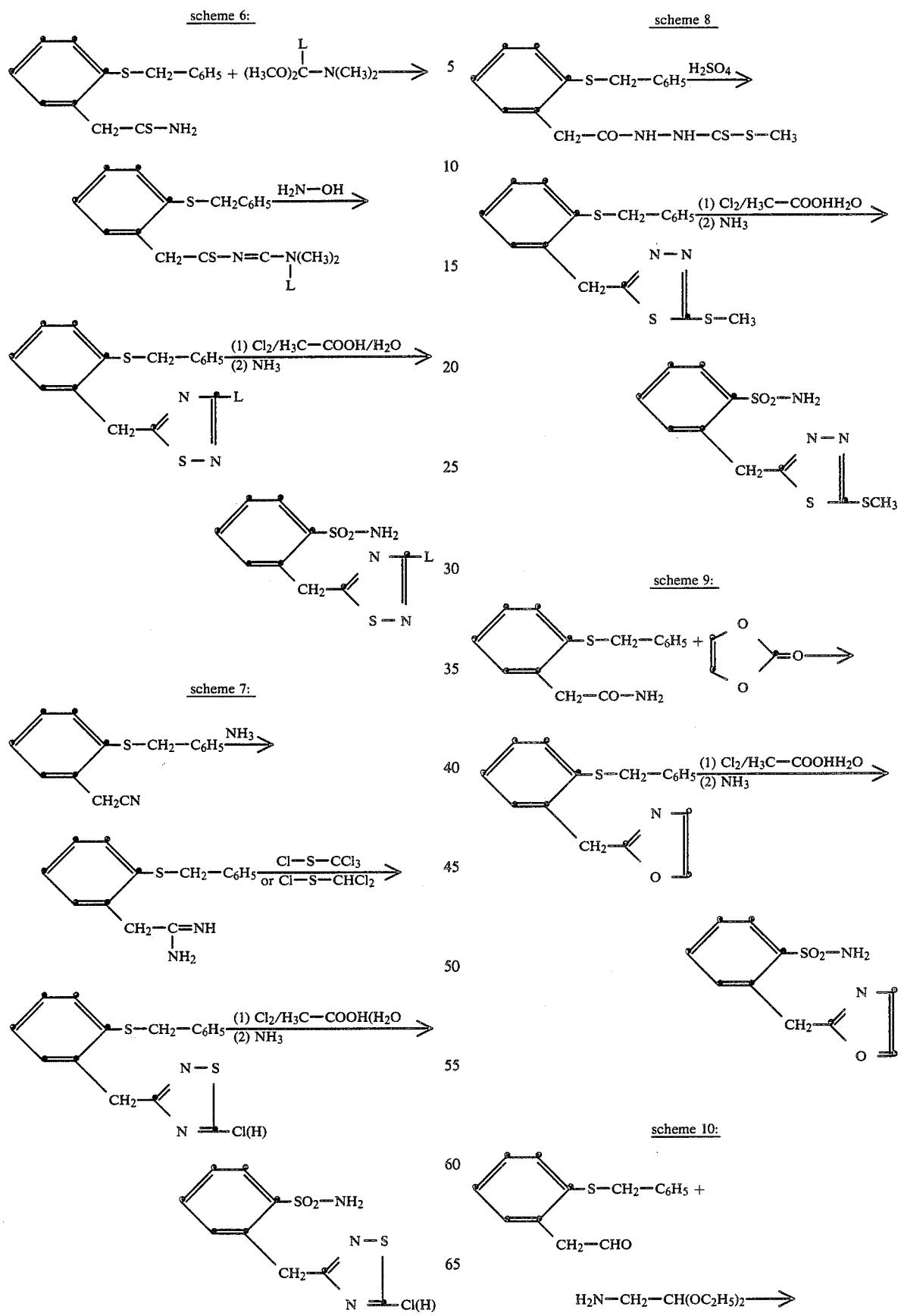

-continued
scheme 10:

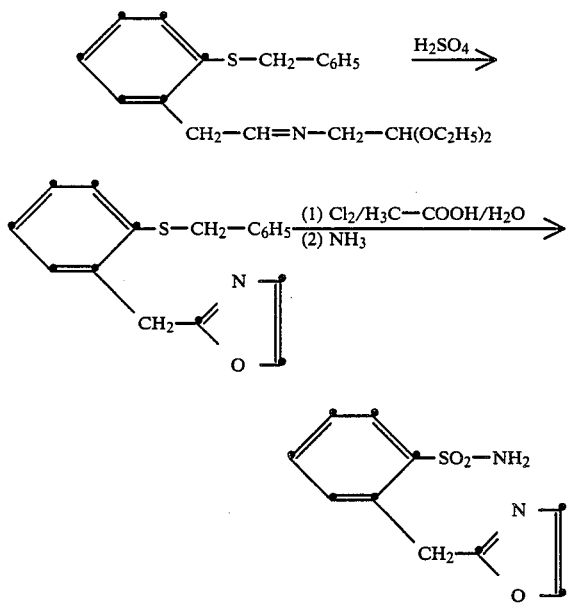

scheme 11:

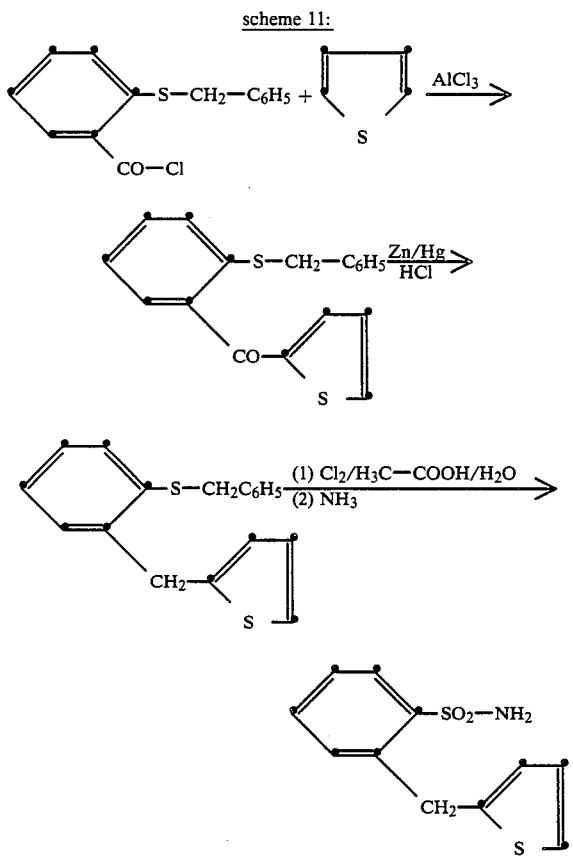

The final products can be isolated by concentrating the reaction mixture and/or evaporating off the solvent, and purified by recrystallising or triturating the solid residue in solvents in which they are not readily soluble, e.g. in an ether, an aromatic hydrocarbon or a chlorinated hydrocarbon.

The compounds of formula I are stable compounds and no protective measures are required for handling them.

When used at low rates of application, the compounds of formula I have good selective growth inhibiting and selective herbicidal properties which make them most suitable for use in crops of useful plants, especially in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of the formula I are effective even when used at very low rates of application.

The compounds of formula I have in addition pronounced growth-regulating, especially growth-inhibiting, properties. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whilst vegetative growth is inhibited.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of applications, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts or higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulations are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich and Vienna, 1981; M. and J. Ash, "Encyclopedia of Surfactants", Vol. I-III, Chemical Publishing Co., New York, 1980-81.

The pesticidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (% = percentage of weight):

Emulsifiable concentrates active ingredient: 1 to 20%, preferably 5 to 10%
surfactant: 5 to 30%, preferably 10 to 20%
liquid carrier: 50 to 94%, preferably 70 to 85%

Dusts active ingredient: 0.1 to 10%, preferably 0.1 to 1%
solid carrier: 99.9 to 90%, preferably 99.9 to 99%

Suspension concentrates active ingredient: 5 to 75%, preferably 10 to 50%
water: 94 to 25%, preferably 88 to 30%
surfactant: 1 to 40%, preferably 2 to 30%

Wettable powders active ingredient: 0.5 to 90%, preferably 1 to 80%
surfactant: 0.5 to 20%, preferably 1 to 15%
solid carrier: 5 to 95%, preferably 5 to 90%

Granulates active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001% The rates of application are normally from 0.01 to 10 kg a.i./ha, preferably from 0.025 to 5 kg a.i./ha.

The compositions may also contain further ingredients such as stabilisers, antifoams, viscosity regulators,

21 binders, tackifiers, as well as fertilisers and other compounds for obtaining special effects.

The invention is illustrated by the following Examples.

PREPARATORY EXAMPLES

Example P1

4,5-Dihydro-2-(2-sulfamoylphenylmethylthio)thiazole (compound 1.1)

With cooling, 7.9 g of 97%, 1,8-diazabicyclo[5.4.-0]undec-7-ene are added to a suspension of 6.2 g of 97% 4,5-dihydro-2-mercaptothiazole in 50 ml of acetonitrile. To the yellow solution so obtained are added 10.3 g of 2-chloromethylbenzenesulfonamide and the reaction mixture is stirred for 1 hour at 20°-25° C. The reaction solution is then diluted with about 1 liter of water. The precipitate is isolated by filtration and dried, affording 11.9 g (76% of theory) of 4,5-dihydro-2-(2-sulfamoylphenylmethylthio)thiazole of m.p. 123°–125° C.

Example P2

2-(2-Sulfamoylphenylmethylthio)pyrimidine (compound 1.5)

With cooling, 7.9 g of 97% 1,8-diazabicyclo[5.4.0]undec-7-ene are added to a suspension of 5.7 g of 98% 2-mercaptopyrimidine in 50 ml of acetonitrile. To the yellowish solution so obtained are added 10.3 g of 2-chloromethylbenzenesulfonamide. The reaction solution is stirred for 70 hours at 20°-22° C. and then diluted with 1 liter of water. The precipitate is isolated by filtration and dried, affording 12.0 g (85% of theory) of 2-(2-sulfamoylphenylmethylthio)pyrimidine of m.p. 128°–130° C.

Example P3

N-[2-(4,5-Dihydrothiazol-2-ylmethylthio)phenylsulfonyl]-N'-(4-methoxy-6-methylpyrimidin-2-yl)urea (compound 2.1)

With cooling, 2.8 g of 1,8-diazabicyclo[5.4.0]undec-7-ene are added to a solution of 5.3 g of 4,5-dihydro-2-(2-sulfamoylphenylmethylthio)thiazole and 4.8 g of N-(4-methoxy-6-methylpyrimidin-2-yl)-O-phenylcarbamate in 50 ml of acetonitrile. The yellow solution so obtained is stirred for 2 days at 20°-25° C. and then 1.7 g of methanesulfonic acid are added, with cooling. Upon the onset of crystallisation the mixture is diluted with 1 liter of water and the crystals are isolated by filtration, washed with ether and dried. Yield: 7.0 g (85% of theory) of N-[2-(4,5-dihydrothiazol-2-ylthiomethyl)phenylsulfonyl]-N'-(4-methoxy-6-methylpyrimidin-2-yl)urea with a melting point of 175°–175° C. (dec.).

Example P4

N-[2-(Pyrimidin-2-ylmethylthio)phenylsulfonyl]-N'-(4-methoxy-6-methyl-1,3,5-triazin-2-yl)urea (compound 2.10)

With cooling, 3.1 g of 1,8-diazabicyclo[5.4.0]undec-7-ene are added to a solution of 5.7 g of 2-(2-sulfamoylphenylmethylthio)pyrimidine and 5.2 g of N-(4-methoxy-6-methyl-1,3,5-triazin-2-yl)-O-phenylcarbamate in 50 ml of acetonitrile. The yellowish solution so obtained is stirred for 50 hours at 20°-25° C. and then 1.9 g of methanesulfonic acid are added. Upon the onset of crystallisation the mixture is diluted with 1 liter of water and the precipitate is isolated by filtration, washed with ether and dried, affording 7.5 g (84% of theory) of N-[2-(pyrimidin-2-ylthiomethyl)phenylsulfonyl]-N'-(4-methoxy-6-methyl-1,3,5-triazin-2-yl)urea with a melting point of 196°–198° C. (dec.).

The intermediates and final products listed in the following table are prepared in corresponding manner.

TABLE 1

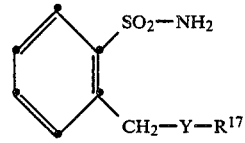

| Compound No. | Y | $R^{17}$ | m.p. [°C.] |
|---|---|---|---|
| 1.1 | S | 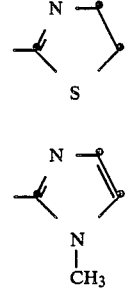 | 123–125 |
| 1.2 | S | 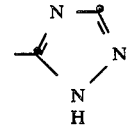 | 182–184 |
| 1.3 | S | 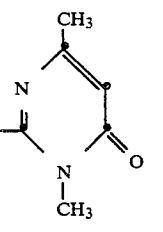 | 188–190 |
| 1.4 | S | 2-pyridinyl | 121–123 |
| 1.4 | S | 2-pyrimidinyl | 128–130 |
| 1.6 | S | 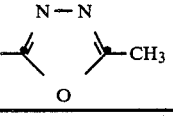 | 194–196 |
| 1.7 | O |  | |

TABLE 2

$$\text{[Structure: benzene ring with } SO_2-NH-CO-NH-C(=N-R^6)(E)(N=R^7) \text{ and } CH_2-Y-R^{17} \text{ substituent]}$$

| Compound No. | E | Y | R¹⁷ | R⁶ | R⁷ | m.p. [°C.] |
|---|---|---|---|---|---|---|
| 2.1 | CH | S | thiazol-2-yl (N,S ring) | CH₃ | OCH₃ | 174–175 (dec.) |
| 2.2 | N | S | thiazol-2-yl (N,S ring) | CH₃ | OCH₃ | 177–179 (dec.) |
| 2.3 | CH | S | 1-methylimidazol-2-yl | CH₃ | OCH₃ | 190–192 (dec.) |
| 2.4 | N | S | 1-methylimidazol-2-yl | CH₃ | OCH₃ | 180–182 (dec.) |
| 2.5 | CH | S | 1H-1,2,4-triazol-3-yl | CH₃ | OCH₃ | 217–218 (dec.) |
| 2.6 | N | S | 1H-1,2,4-triazol-3-yl | CH₃ | OCH₃ | 189–191 (dec.) |
| 2.7 | CH | S | 2-pyridinyl | CH₃ | OCH₃ | 199–201 (dec.) |
| 2.8 | CH | S | 2-pyrimidinyl | CH₃ | CH₃ | 217–219 (dec.) |
| 2.9 | CH | S | 2-pyrimidinyl | CH₃ | OCH₃ | 211–213 (dec.) |
| 2.10 | N | S | 2-pyrimidinyl | CH₃ | OCH₃ | 196–198 (dec.) |
| 2.11 | CH | S | 1,4-dimethyl-6-oxo-pyrimidin-2-yl | CH₃ | OCH₃ | 226–228 (dec.) |
| 2.12 | N | S | 1,4-dimethyl-6-oxo-pyrimidin-2-yl | CH₃ | OCH₃ | 203–205 (dec.) |

TABLE 2-continued

[Structure: benzene ring with SO₂—NH—CO—NH—C(=N—R⁶)(E)(=N—R⁷) substituent, and CH₂—Y—R¹⁷ substituent]

| Compound No. | E | Y | R¹⁷ | R⁶ | R⁷ | m.p. [°C.] |
|---|---|---|---|---|---|---|
| 2.13 | CH | O | 3,5-dimethyl-1,3,4-oxadiazole | CH₃ | OCH₃ | |
| 2.14 | N | O | 3,5-dimethyl-1,3,4-oxadiazole | CH₃ | OCH₃ | |
| 2.15 | CH | S | 4,6-dimethylpyrimidin-2-yl | CH₃ | OCH₃ | 217–219 (dec.) |
| 2.16 | N | S | 4,6-dimethylpyrimidin-2-yl | CH₃ | OCH₃ | 188–190 (dec.) |
| 2.17 | CH | S | 4-chlorophenyl | CH₃ | OCH₃ | 217–219 (dec.) |
| 2.18 | CH | S | —CH₂—(4-chlorophenyl) | CH₃ | OCH₃ | 142–145 |
| 2.19 | N | S | 4-chlorophenyl | CH₃ | OCH₃ | 202–204 |
| 2.20 | N | S | —CH₂—(4-chlorophenyl) | CH₃ | OCH₃ | 170–173 |
| 2.21 | N | S | benzothiazol-2-yl | CH₃ | OCH₃ | 198–199 |
| 2.22 | CH | S | benzothiazol-2-yl | CH₃ | OCH₃ | 212–214 (dec.) |

TABLE 2-continued

Structure:

Benzene ring with SO₂—NH—CO—NH—C(=N—R⁶)(=N—R⁷) with E bridge, and CH₂—Y—R¹⁷ substituent on benzene ring.

| Compound No. | E | Y | R¹⁷ | R⁶ | R⁷ | m.p. [°C] |
|---|---|---|---|---|---|---|
| 2.23 | N | S | benzoxazol-2-yl | $CH_3$ | $OCH_3$ | 198–199 (dec.) |
| 2.24 | CH | S | benzoxazol-2-yl | $CH_3$ | $OCH_3$ | 198–199 (dec.) |
| 2.25 | N | S | 4,6-dimethylpyrimidin-2-yl | $-N(CH_3)_2$ | $-OCH_3$ | 200–205 |
| 2.26 | N | S | $-CH_2-$(furan-2-yl) | $CH_3$ | $OCH_3$ | 128–129 |
| 2.27 | CH | S | $-CH_2-$(furan-2-yl) | $CH_3$ | $OCH_3$ | 141–143 |
| 2.28 | CH | S | 4,6-dimethylpyrimidin-2-yl | $OCH_3$ | $OCH_3$ | 215–220 |
| 2.29 | CH | S | 4,6-dimethylpyrimidin-2-yl | $-CH_2-OCH_3$ | $OCH_3$ | 187–189 |
| 2.30 | CH | O | 2,4-dichlorophenyl | $CH_3$ | $CH_3$ | 221–222 |
| 2.31 | N | O | 2,4-dichlorophenyl | $CH_3$ | $OCH_3$ | 195–196 |

FORMULATION EXAMPLES

Example F1

Formulation Examples for compounds of formula I (percentages are by weight)

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glycol ether (78 moles of ethylene oxide) | 3% |
| water | 91% |

BIOLOGICAL EXAMPLES

Example B1

Preemergence herbicidal action

Plastic pots are filled with expanded vermiculite (density: 0.135 g/cm$^3$, water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis*, *Agrostis tenuis*, *Stellaria media* and *Digitaria sanguinalis*. The pots are then kept in a climatic chamber at 20° C., an illumination of about 20 lux and a relative humidity of 70%. During the germinating phase of 4 to 6 days, the pots are covered with lightpermeable material and watered with deionised water to increase the local humidity. After the 5th day, 0.5% of a commercial liquid fertiliser (Greenzit ®, ex Ciba-Geigy) is added to the water. The test is evaluated 12 days after sowing and the action on the plants is assessed according to the following rating:

1: plants have not emerged or are totally withered
2–3: very pronounced action
4–6: medium action
7–8: weak action
9: no action (as untreated controls).

Preemergence action:
Concentration of the test compound emulsion: 70.8 ppm

| Test plant Compound No. | Nasturtium | Stellaria | Agrostis | Digitaria |
|---|---|---|---|---|
| 2.1 | 1 | 1 | 1 | 1 |
| 2.2 | 1 | 1 | 1 | 1 |
| 2.3 | 1 | 2 | 1 | 3 |
| 2.4 | 2 | 2 | 2 | 5 |
| 2.5 | 2 | 2 | 2 | 3 |
| 2.6 | 4 | 4 | 4 | 7 |
| 2.7 | 1 | 1 | 1 | 1 |
| 2.9 | 1 | 1 | 1 | 1 |
| 2.10 | 1 | 1 | 1 | 2 |
| 2.11 | 2 | 2 | 2 | 3 |
| 2.12 | 2 | 7 | 3 | 8 |
| 2.15 | 2 | 2 | 2 | 2 |
| 2.16 | 1 | 2 | 2 | 2 |

-continued

Preemergence action:
Concentration of the test compound emulsion: 70.8 ppm

| Test plant Compound No. | Nasturtium | Stellaria | Agrostis | Digitaria |
|---|---|---|---|---|
| 2.17 | 2 | 2 | 2 | 2 |
| 2.18 | 1 | 1 | 1 | 2 |
| 2.19 | 1 | 3 | 3 | 6 |
| 2.20 | 2 | 2 | 3 | 3 |
| 2.21 | 2 | 2 | 2 | 3 |
| 2.22 | 2 | 4 | 1 | 5 |
| 2.23 | 2 | 2 | 2 | 2 |
| 2.24 | 1 | 1 | 1 | 2 |
| 2.25 | 1 | 2 | 1 | 3 |
| 2.26 | 1 | 1 | 1 | 3 |
| 2.27 | 2 | 2 | 1 | 2 |
| 2.28 | 3 | 2 | 2 | 3 |
| 2.29 | 3 | 2 | 2 | 4 |
| 2.31 | 2 | 2 | 5 | 3 |

Example B2

Growth inhibition of tropical cover crops

The test plants (centrosema plumieri and centrosema pubescens) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

Example B3

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of the formula I until thoroughly wetted. The rate of application corresponds to 100 g a.i. per hectare. Evaluation is made about 5 weeks after application. Compared with untreated controls, the compounds of the formula I markedly increase the number and weight of the harvested siliques on the leading shoot.

Example B4

Growth inhibition of cereals

Summar barley (Hordeum vulgare) and summer rye (Secale) are sown in sterilised soil in plastic beakers in a greenhouse and watered as required. The cereal shoots are treated about 21 days after sowing with an aqueous spray mixture of a compound of the formula I. The concentration corresponds to 100 g of active ingredient per hectare. Evaluation of the growth of the cereals is made 21 days after application. A comparison with untreated controls shows that the growth of cereal plants treated with compounds of the formula I is significantly reduced (60-90% of the controls) and that the diameter of the stalks has in some cases increased.

Example B5

Growth inhibition of grasses

Seeds of the grasses Lolium perenne, Poa pratensis, Festuca ovina, Dactylis glomerate and Cynodon dactylon are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of the formula I. The concentration of test compound corresponds to a rate of application of up to 100 g a.i. per hectare. The growth of the grasses is evaluated 21 days after application. The compounds of formula I effect a reduction in new growth in the range of 10-30% in comparison with untreated controls.

What is claimed is:

1. A substituted N-phenylsulfonyl-N'-pyrimidinylurea of the formula

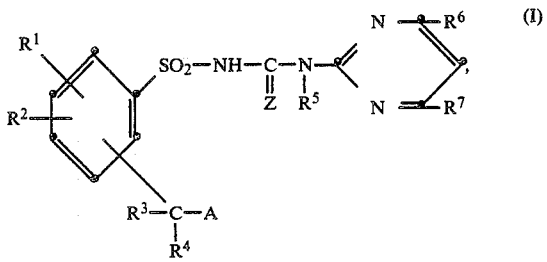

wherein $R^1$ is hydrogen, halogen, nitro, cyano, $C_1$-$C_4$alkyl, $C_1$-$C_4$haloalkyl, $C_1$-$C_4$alkoxy, $C_1$-$C_4$alkylthio, $C_1$-$C_4$alkylsulfonyl, $C_1$-$C_4$alkylsulfinyl, —CO—$R^8$, —$NR^9R^{10}$, —CO—$NR^{11}R^{12}$ or —$SO_2$—$NR^{13}R^{14}$, $R^2$ is hydrogen, halogen, $C_1$-$C_4$alkyl, $C_1$-$C_4$alkoxy, $C_1$-$C_4$alkylthio, $C_1$-$C_4$alkylsulfinyl or $C_1$-$C_4$alkylsulfonyl, $R^3$ is hydrogen, $C_1$-$C_4$alkyl, $C_1$-$C_4$haloalkyl or cyano, $R^4$ is hydrogen or $C_1$-$C_4$alkyl, $R^5$ is hydrogen, $C_1$-$C_4$alkyl or $C_1$-$C_4$alkoxy, $R^6$ and $R^7$ are each independently hydrogen, halogen, $C_1$-$C_4$alkyl, $C_1$-$C_4$alkoxy, $C_1$-$C_4$haloalkyl, $C_1$-$C_4$haloalkoxy, $C_1$-$C_4$alkylthio, $C_1$-$C_4$haloalkylthio, $C_2$-$C_4$alkoxyalkyl, $C_3$-$C_6$cycloalkyl or —$NR^{15}R^{16}$, $R^8$ is hydrogen, $C_1$-$C_4$alkyl, $C_1$-$C_4$haloalkyl, $C_1$-$C_4$alkoxy, $C_1$-$C_4$haloalkoxy, $C_1$-$C_4$alkylthio or $C_2$-$C_4$alkoxyalkoxy, $R^9$, $R^{10}$, $R^{11}$, $R^{12}$, $R^{13}$, $R^{14}$, $R^{15}$ and $R^{16}$ are each independently hydrogen or $C_1$-$C_4$alkyl, A is a radical —Y—$(CH_2)_n$—$R^{17}$ or

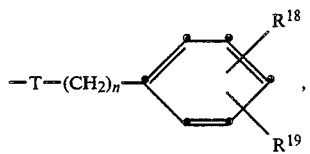

$R_{17}$ is a radical selected from

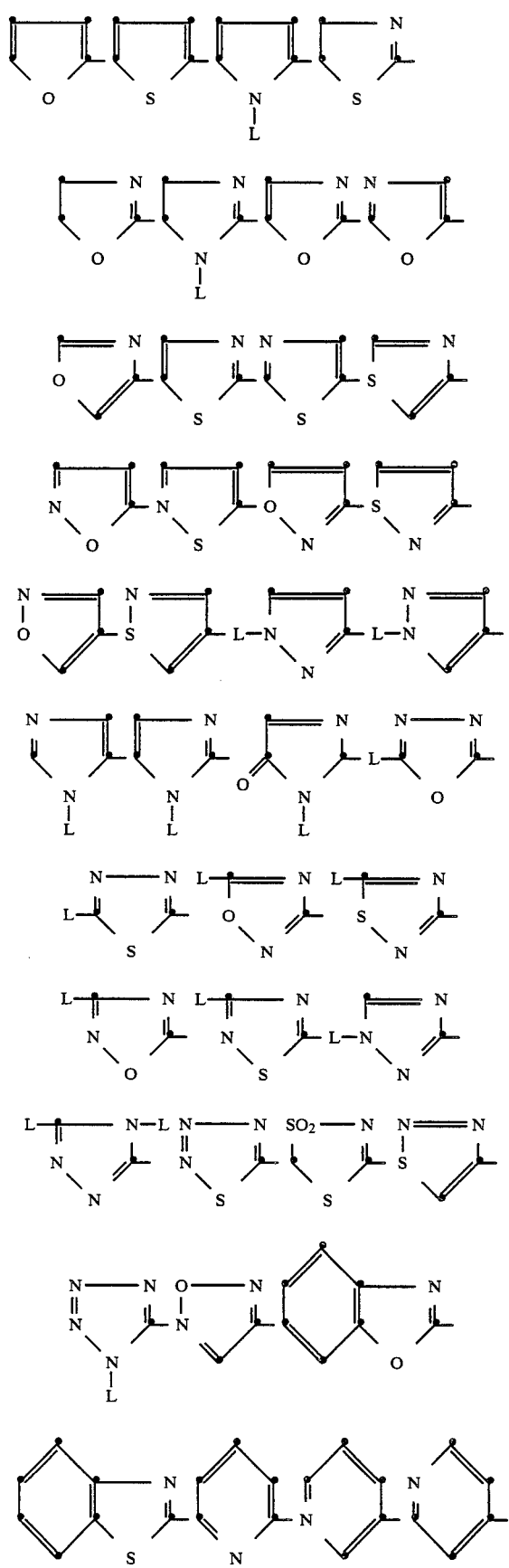

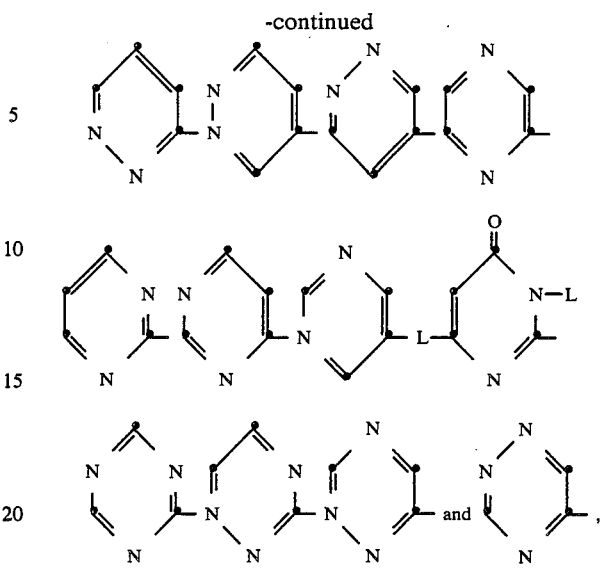

L is hydrogen or $C_1$-$C_4$ alkyl,
$R^{18}$ and $R^{19}$ are each independently hydrogen, halogen, $C_1$-$C_4$alkyl, $C_1$-$C_4$haloalkyl, $C_1$-$C_4$alkoxy, $C_1$-$C_4$alkoxy, $C_1$-$C_4$haloalkoxy, nitro or cyano,
Y is oxygen, sulfur or a direct bond,
T and Z are each independently oxygen or sulfur, and n is 0 or 1,
or a salt thereof.

2. A compound according to claim 1, wherein Z is oxygen.

3. A compound according to claim 1, wherein $R^1$ is hydrogen.

4. A compound according to claim 1, wherein $R^2$ is hydrogen.

5. A compound according to claim 1, wherein $R^3$ is hydrogen.

6. A compound according to claim 1, wherein $R^4$ is hydrogen.

7. A compound according to claim 1, wherein $R^5$ is hydrogen.

8. A compound according to claim 1, wherein $R^6$ and $R^7$ are each independently halogen, $C_1$-$C_4$alkyl, $C_1$-$C_4$alkoxy, di($C_1$-$C_4$)alkylamino or $C_1$-$C_4$haloalkoxy and together contain not more than 4 carbon atoms.

9. A compound according to claim 1, wherein A is the —Y—(CH$_2$)$_n$—$R^{17}$ group.

10. A compound according to claim 9, wherein n is 0.

11. A compound according to claim 10, wherein A is the —S—$R^{17}$ radical.

12. A compound according to claim 11, wherein —S—$R^{17}$ is a radical selected from the group consisting of 4,5-dihydrothiazol-2-ylthio, 3-methylimidazol-2-ylthio, 1,3,4-triazol-2-ylthio, pyridin-2-yl-thio, pyrimidin-2-ylthio or 3H-2,6-dimethyl-3-oxopyrimidin-2-ylthio.

13. A compound according to claim 1, wherein Z is oxygen, $R^1$, $R^2$, $R^3$, $R^4$ and $R^5$ are hydrogen, and each of $R^6$ and $R^7$ is independently halogen, $C_1$-$C_4$alkyl, $C_1$-$C_4$alkoxy, di($C_1$-$C_4$)alkylamino or $C_1$-$C_4$haloalkoxy, and together contain not more than 4 carbon atoms.

14. A compound according to claim 1, wherein Z is oxygen, $R^1$, $R^2$, $R^3$, $R^4$ and $R^5$ are hydrogen, each of $R^6$ and $R^7$ is independently halogen, $C_1$-$C_4$alkyl, $C_1$-$C_4$alkoxy, di($C_1$-$C_4$)alkylamino or $C_1$-$C_4$haloalkoxy, and together contain not more than 4 carbon atoms, and A is the —S—$R^{17}$ radical.

15. A compound according to claim 1, wherein Z is oxygen, $R^1$, $R^2$, $R^3$, $R^4$ and $R^5$ are hydrogen, each of $R^6$ and $R^7$ is independently halogen, $C_1$–$C_4$alkyl, $C_1$–$C_4$alkoxy, di($C_1$–$C_4$)alkylamino or $C_1$–$C_4$haloalkoxy, and together contain not more than 4 carbon atoms, and A is a radical selected from the group consisting of 4,5-dihydrothiazol-2-ylthio, 3-methylimidazol-2-ylthio, 1,3,4-triazol-2-ylthio, pyridin-2-ylthio, pyrimidin-2-ylthio or 3H-2,6-dimethyl-3-oxopyrimidin-2-ylthio.

16. A compound according to claim 1, which is selected from the group consisting of
N-[2-(4,5-dihydrothiazol-2-ylthiomethyl)phenylsulfonyl]-N-'-(4-methoxy-6-methylpyrimidin-2-yl)urea, and
N-[2-(pyrimidin-2-ylthiomethyl)phenylsulfonyl]-N'-(4-methoxy-6-methylpyrimidin-2-yl)urea.

17. A herbicidal and plant growth inhibiting composition which contains at least one substituted N-phenylsulfonyl-N'-pyrimidinylurea of claim 1, together with a carrier and/or other adjuvants.

18. A method of controlling undesired plant growth, which comprises applying an effective amount of a compound of the formula I according to claim 1, or of a composition containing such a compound to the plant or the locus thereof.

19. A method of inhibiting plant growth, which comprises applying an effective amount of a compound of the formula I according to claim 1, or of a composition containing such a compound to the plant or the locus thereof.

20. A method of influencing plant growth for increasing yield, which comprises applying an effective amount of a compound of the formula I according to claim 1, or of a composition containing such a compound of the plant or the locus thereof.

21. A method according to claim 18 of selectively controlling weeds pre- or postemergence in crops of useful plants, which method comprises applying an effective amount of a compound of the formula I, or of a composition containing such a compound to the plant or the locus thereof.

22. A method according to claim 19 of inhibiting plant growth beyond the 2-leaf stage preemeergence, which method comprises applying an effective amount of a compound of the formula I, or of a composition containing such a compound to the plant or the locus thereof.

* * * * *